US008153604B2

(12) United States Patent
Deen et al.

(10) Patent No.: US 8,153,604 B2
(45) Date of Patent: Apr. 10, 2012

(54) CNS-TUMOR TREATMENT METHOD AND COMPOSITION

(75) Inventors: Dennis F. Deen, Petaluma, CA (US); William H. Frey, II, White Bear Lake, MN (US); Sergei Gryaznov, San Mateo, CA (US)

(73) Assignees: Geron Corporation, Menlo Park, CA (US); HealthPartners Research Foundation, Bloomington, MN (US); The Regents of the University of California, Oakland, CA (US)

( * ) Notice: Subject to any disclaimer, the term of this patent is extended or adjusted under 35 U.S.C. 154(b) by 496 days.

(21) Appl. No.: 12/297,301

(22) PCT Filed: Apr. 23, 2007

(86) PCT No.: PCT/US2007/009839
§ 371 (c)(1),
(2), (4) Date: Feb. 24, 2009

(87) PCT Pub. No.: WO2007/127163
PCT Pub. Date: Nov. 8, 2007

(65) Prior Publication Data
US 2009/0175801 A1 Jul. 9, 2009

Related U.S. Application Data

(60) Provisional application No. 60/794,873, filed on Apr. 24, 2006.

(51) Int. Cl.
*A61K 31/70* (2006.01)
*C07H 21/02* (2006.01)
*C07H 21/04* (2006.01)
*C12Q 1/68* (2006.01)

(52) U.S. Cl. .................. 514/44 A; 536/23.1; 536/24.1; 536/24.5; 435/375; 435/377

(58) Field of Classification Search .................. None
See application file for complete search history.

(56) References Cited

U.S. PATENT DOCUMENTS

| 5,583,016 | A | 12/1996 | Villeponteau et al. |
| 5,624,898 | A | 4/1997 | Frey |
| 5,656,638 | A | 8/1997 | Gaeta et al. |
| 5,695,932 | A | 12/1997 | West et al. |
| 5,760,062 | A | 6/1998 | Gaeta et al. |
| 5,767,278 | A | 6/1998 | Gaeta et al. |
| 5,770,613 | A | 6/1998 | Gaeta et al. |
| 5,863,936 | A | 1/1999 | Gaeta et al. |
| 5,952,490 | A | 9/1999 | Hanecak et al. |
| 6,180,603 | B1 | 1/2001 | Frey |
| 6,261,836 | B1 | 7/2001 | Cech et al. |
| 6,294,153 | B1 | 9/2001 | Modi |
| 6,313,093 | B1 | 11/2001 | Frey |
| 6,331,399 | B1 | 12/2001 | Monia et al. |
| 6,368,789 | B1 | 4/2002 | West et al. |
| 6,410,046 | B1 * | 6/2002 | Lerner .................... 424/434 |
| 6,444,650 | B1 | 9/2002 | Cech et al. |
| 6,468,983 | B2 * | 10/2002 | Silverman et al. .......... 514/44 A |
| 6,475,523 | B1 | 11/2002 | Staniforth et al. |
| 6,548,298 | B2 | 4/2003 | Villeponteau et al. |
| 6,608,036 | B1 | 8/2003 | Gryaznov et al. |
| 6,780,508 | B1 | 8/2004 | Caponetti et al. |
| 6,794,357 | B1 | 9/2004 | Backstrom et al. |
| 6,835,826 | B2 | 12/2004 | Gryaznov et al. |
| 7,001,818 | B2 | 2/2006 | Tsuchiya et al. |
| 7,022,311 | B1 | 4/2006 | Ohkuma et al. |
| 7,067,497 | B2 | 6/2006 | Hanecak et al. |
| 7,138,383 | B2 | 11/2006 | Gryaznov et al. |
| 7,563,618 | B2 * | 7/2009 | Gryaznov et al. ............. 435/375 |
| 7,998,938 | B2 * | 8/2011 | Moore et al. ................ 514/44 R |
| 2003/0072793 | A1 | 4/2003 | Frey |
| 2005/0113325 | A1 | 5/2005 | Gryaznov et al. |
| 2006/0009636 | A1 | 1/2006 | Gryaznov et al. |

FOREIGN PATENT DOCUMENTS

| WO | WO 91/07947 A1 | 6/1991 |
| WO | WO 94/08053 A1 | 4/1994 |
| WO | WO 98/28442 A1 | 7/1998 |
| WO | WO 00/33814 A2 | 6/2000 |
| WO | WO 01/18015 A1 | 3/2001 |
| WO | WO 02/086105 A1 | 10/2002 |

OTHER PUBLICATIONS

Dhanda et al., Drug Delivery Technology, vol. 5(4):64-72, 2005.*
Aggarwal, R. et al., "The assessment of topical nasal drug distribution," *Clin. Otolaryngol. Allied Sci.*, 29:201-5 (2004).
Blackburn, E., "Switching and signaling at the telomere," *Cell*, 106(6):661-73 (2001).
Bobo, R. et al., "Convection-enhanced delivery of macromolecules in the brain," *Proc. Natl. Acad. Sci. USA*, 91(6):2076-80 (1994).
Boiardi, A. et al., "Systemic temozolomide combined with loco-regional mitoxantrone in treating recurrent glioblastoma," *Journal of Neuro-Oncology*, 75(2):215-220 (2005).
CBTRUS: Central Brain Tumor Registry of the United States, www.cbtrus.org/2005-2006/tables/2006.table19.pdf (accessed Jan. 24, 2006).
Chen, J. et al., "Secondary structure of vertebrate telomerase RNA," *Cell*, 100:503-14 (2000).
Chong, E. et al., "Telomerase expression in gliomas including the nonastrocytic tumors," *Hum. Pathol.*, 29(6):599-603 (1998).
Djupesland, P. et al., "Breath actuated device improves delivery to target sites beyond the nasal valve," *The Laryngoscope*, 116:466-72 (2006).
Feng, J. et al., "The RNA component of human telomerase," *Science*, 269:1236-41 (1995).

(Continued)

*Primary Examiner* — Sean McGarry
(74) *Attorney, Agent, or Firm* — King & Spalding LLP; Peter J. Dehlinger; LeeAnn Gorthey

(57) ABSTRACT

A method, aerosol composition, and aerosolizing device for treating a brain tumor in a subject are disclosed. The method includes intranasally administering to the subject, an amount of a telomerase inhibitor, such as an oligonucleotide telomerase inhibitor, effective to inhibit growth of the tumor in the subject.

8 Claims, 5 Drawing Sheets

OTHER PUBLICATIONS

Gowan, S. et al., "A G-quadruplex-interactive potent small-molecule inhibitor of telomerase exhibiting in vitro and in vivo antitumor activity," *Mol. Pharmacol.*, 61(5):1154-62 (2002).

Greider, C. & Blackburn, E., "Identification of a specific telomere terminal transferase activity in *Tetrahymena* extracts," *Cell*, 43:405-13 (1985).

Groothuis, D., "The blood-brain and blood-tumor barriers: a review of strategies for increasing drug delivery," *Neuro. Oncology*, 2(1):45-59 (2000).

Hiyama et al., "Activation of telomerase in human lymphocytes and hematopoietic progenitor cells," *Journal of Immunology*, 155(8):3711-3715 (1995).

Holt, S. et al., "Multiple pathways for the regulation of telomerase activity," *European Journal of Cancer*, 33(5):761-766(1997).

Huynh, G. et al., "Barriers to carrier mediated drug and gene delivery to brain tumors," *Journal of Controlled Release*, 110(2):236-59 2006.

Kawakami, K. et al. "Distribution kinetics of targeted cytotoxin in glioma by bolus or convection-enhanced delivery in a murine model," *Journal of Neurosurgery*, 101(6):1004-11 (2004).

Kim, C. et al., "Specific association of human telomerase activity with immortal cells and cancer ," *Science*, 266:2011-205 (1994).

Langford, L. et al., "Telomerase activity in human brain tumours," *Lancet*, 346(8985):1267-1268 (1995).

Le, S. et al., "Telomerase activity in human gliomas," *Neurosurgery*, 42(5):1120-1124 (1998).

Legler, J. et al., "Cancer surveillance series: brain and other central nervous system cancers: recent trends in incidence and mortality," *Journal of the National Cancer Institute*, 91(16):1382-90 (1999).

Lidar, Z. et al., "Convection-enhanced delivery of paclitaxel for the treatment of recurrent malignant glioma: a phase I/II clinical study," *J. Neurosurg.*, 100(3):472-9 (2004).

MacKay, J. et al., "Distribution in brain of liposomes after convection enhanced delivery; modulation by particle charge, particle diameter, and presence of steric coating," *Brain Research*, 1035(2):139-53 (2005).

Mamot, C. et al., "Extensive distribution of liposomes in rodent brains and brain tumors following convection-enhanced delivery," *Journal of Neurooncology*, 68(1):1-9 (2004).

Morii, K. et al., "Expression of telomerase RNA, telomerase activity, and telomere length in human gliomas," *Biochemical and Biophysical Research Communications*, 239(3):830-4 (1997).

Nakamura, T. et al., "Telomerase catalytic subunit homologs from fission yeast and human," *Science*, 277:955-9 (1997).

Ozawa, T. et al., "Antitumor effects of specific telomerase inhibitor GRN163 in human glioblastoma xenografts," *Neuro-Oncology*, 6(3):218-26 (2004).

Ozawa, T. et al., "In vivo evaluation of the boronated porphyrin TABP-1 in U-87 MG intracerebral human glioblastoma xenografts," *Molecular Pharmaceutics*, 1(5):368-74 (2004).

Ozawa, T. et al., "Toxicity, biodistribution, and convection-enhanced delivery of the boronated porphyrin BOPP in the 9L intracerebral rat glioma model," *Int. J. Radiation Oncology Biol. Phys.*, 63(1):247-52 (2005).

Pascolo, E. et al., "Mechanism of human telomerase inhibition by BIBR1532, a synthetic, non-nucleosidic drug candidate," *The Journal of Biological Chemistry*, 277(18):15566-72 (2002).

Pongracz, K. & Gryaznov, S., "Oligonucleotide N3'->P5' thiophosporamidates: synthesis and properties," *Tetrahedron Letters*, 40:7661-4 (1999).

Saito, R et al., "Convection-enhanced delivery of tumor necrosis factor-related apoptosis-inducing ligand with systemic administration of temozolomide prolongs survival in an intracranial glioblastoma xenograft model," *Cancer Research*, 64(19):6858-62 (2004).

Saito, R. et al., "Convection-enhanced delivery of Ls-TPT enables an effective, continuous, low-dose chemotherapy against malignant glioma xenograft model," *Neuro-Oncology*, 8(3):205-14 (2006).

Sano, T. et al., "Telomerase activity in 144 brain tumours," *British Journal of Cancer*, 77(10):1633-7 (1998).

Shay, J. & Wright, W., "Telomerase activity in human cancer," *Current Opinion in Oncology*, 8:66-71 (1996).

Shin-Ya, K. et al., "Telomestatin, a novel telomerase inhibitor from *Streptomyces anulatus*," *J. Am. Chem. Soc*. 123(6):1262-3 (2001).

Surawicz, T. et al., "Brain tumor survival: results from the National Cancer Database," *Journal of Neuro-Oncology*, 40(2):151-60 (1998).

Ward, R. & Autexier, C., "Pharmacological telomerase inhibition can sensitize drug-resistant and drug-sensitive cells to chemotherapeutic treatment," *Molecular Pharmacology*, 68:779-86 (2005).

Alcalay, R. et al., "Intranasal administration of NAP, a neuroprotective peptide, decreases anxiety-like behavior in aging mice in the elevated plus maze," *Neuroscience Letters*, 361:128-31 (2004).

Banks, W. et al., "Brain uptake of the glucagon-like peptide-1 antagonist exendin(9-39) after intranasal administration," *The Journal of Pharmacology and Experiemntal Therapeutics*, 309(2):469-75 (2004).

Benedict, C. et al., "Differential sensitivity of men and women to anorexigenic and memory-improving effects of intranasal insulin," *J. Clin. Endocrinol. Metab.*, 93(4):1339-44 (2008).

Benedict, C. et al., "Intranasal insulin improves memory in humans," *Neuropsychopharmacology*, 32:239-43 (2007).

Benedict, C. et al., "Intranasal insulin improves memory in humans: superiority of insulin aspart," *Psychoneuroendocrinology*, 29:1326-34 (2004).

Born, J. et al., "Sniffing neuropeptides: a transnasal approach to the human brain," *Nature Neuroscience*, 5(6):514-6 (2002).

Capsoni, S. et al., "Nerve growth factor and galantamine ameliorate early signs of neurodegeneration in anti-nerve growth factor mice," *Proc. Natl. Acad. Sci. USA*, 99(19):12432-7 (2002).

Da Fonseca, C. et al., "Recent advances in the molecular genetics of malignant gliomas disclose targets for antitumor agent perillyl alcohol," *Surgical. Neurology*, 65:S1:2-S1:9 (2006).

De Rosa, R. et al., "Intranasal administration of nerve growth factor (NGF) rescues recognition memory deficits in AD11 anti-NGF transgenic mice," *Proc. Natl. Acad. Sci. USA*, 102(10):3811-6 (2005).

Draghia, R. et al., "Gene delivery into the central nervous system by nasal instillation in rats," *Gene Therapy*, 2:418-423 (1995).

During, M. et al., "Glucagon-like peptide-1 receptor is involved in learning and neuroprotection," *Nature Medicine*, 9(9):1173-9 (2003).

Gozes, I. et al., "Activity-dependent neurotrophic factor: intranasal administration of femtomolar-acting peptides improve performance in a water maze," *The Journal of Pharmacology and Experiemntal Therapeutics*, 293(3):1091-8 (2000).

Hallschmid, M. et al., "Intranasal insulin reduces body fat in men but not in women," *Diabetes*, 53:3024-3029 (2004).

Hallschmid, M. et al., "Obese men respond to cognitive but not to catabolic brain insulin signaling," *International Journal of Obesity*, 32(2):275-82 (2008).

Han, In-K. et al., "Enhanced brain targeting efficiency of intranasally administered plasmid DNA: an alternative route for brain gene therapy," *J. Mol. Med.*, 85(1):75-83 (2007).

Hanson, L. et al., "Intranasal administration of hypocretin 1 (orexin A) bypasses the blood-brain barrier & targets the brain: a new strategy for the treatment of narcolepsy," *Drug Delivery Tech.*, 4(4):66-71 (2004).

Hashizume, R. et al., "New therapeutic approach for brain tumors: intranasal delivery of telomerase inhibitor GRN163," *Neuro-Oncology*, 10:112-20 (2008).

Jerusalmi, A. et al., "Effect of intranasal administration of Semliki Forest virus recombinant particles expressing reporter and cytokine genes on the progression of experimental autoimmune encephalomyelitis," *Molecular Therapy*, 8(6):886-94 (2003).

Jin, K. et al., "Cerebral neurogenesis is induced by intranasal administration of growth factors," *Ann. Neurol.*, 53:405-409 (2003).

Kosfeld, M. et al., "Oxytocin increases trust in humans," *Nature*, 435:673-6 (2005).

Laing, J. et al., "Intranasal administration of the growth-compromised HSV-2 vector DeltaRR prevents kainate-induced seizures and neuronal loss in rats and mice," *Mol. Ther.*, 13(5):870-881 (2006).

Lemiale, F. et al., "Enhanced mucosal immunoglobulin a response of intranasal adenoviral vector human immunodeficiency virus vaccine and localization in the central nervous system," *Journal of Virology*, 77(18):10078-10087 (2003).

Liu, Xin-F. et al., "The window of opportunity for treatment of focal cerebral ischemic damage with noninvasive intranasal insulin-like growth factor-1 in rats," *Journal of Stroke and Cerebrovascular Diseases*, 13(1):16-23 (2004).

Reger, M. et al., "Intranasal insulin administration dose-dependently modulates verbal memory and plasma amyloid-β in memory-impaired older adults," *Journal of Alzheimer's Disease*,. 13(3):323-31 (2008).

Reger, M. et al., "Effects of intranasal insulin on cognition in memory-impaired older adults: modulation by APOE genotype," *Neurobiology of Aging*, 27(3):451-458 (2006).

Reger, M. et al., "Intranasal insulin improves cognition and modulates β-amyloid in early AD," *Neurology*, 70:440-8 (2008).

Ross, T.M. et al., "Intranasal administration of interferon beta bypasses the blood-brain barrier to target the central nervous system and cervical lymph nodes: a non-invasive treatment strategy for multiple sclerosis," *Journal of Neuroimmunology*, 151:66-77 (2004).

Schulz, C. et al., "Central nervous and metabolic effects of intranasally applied leptin," *Endocrinology*, 145(6):2696-701 (2004).

Shimizu, H. et al., "Inhibition of appetite by nasal leptin administration in rats," *International Journal of Obesity*, 29:858-63 (2005).

Shingaki, T. et al., "Transnasal delivery of anticancer drugs to the brain tumor. A new strategy for brain tumor chemotherapy," *Drug Delivery System*, 14(5):365-71 (1999).

Thorne, R. et al., "Delivery of insulin-like growth factor-1 to the rat brain and spinal cord along olfactory and trigeminal pathways following intranasal administration," *Neuroscience*, 127:481-96 (2004).

Thorne, R. et al., "Delivery of interferon-β to the monkey nervous system following intranasal administration," *Neuroscience*, 152(3):785-97 (2008).

Wang, D. et al., "Study on brain targeting of raltitrexed following intranasal administration in rats," *Cancer Chemother. Pharmacol.*, 57(1):97-104 (2005).

Wang, F. et al., "Intranasal delivery of methotrexate to the brain in rats bypassing the blood-brain barrier," *Drug Delivery Technology*, 4(1):48-55 (2004).

Yamada, K. et al., "Nose-to-brain delivery of TS-002, prostaglandin $D_2$ analogue," *Journal of Drug Targeting*, 15(1):59-66 (2007).

Yu, Yue-P. et al., "Intranasal recombinant human erythropoietin protects rats against focal cerebral ischemia," *Neuroscience Letters*, 387:5-10 2005.

Asai, A. et al., "A novel telomerase template antagonist (GRN163) as a potential anticancer agent", *Cancer Research*, 63:3931-3939 (2003).

The International Search report for PCT application for PCT application PCT/US2007/009839, search report dated Oct. 23, 2007, 2 pages (2007).

Gryaznov,S. et al., "Oligonucleotide N3' —> P5' thiophosphoramidate telomerase template antagonists as potential anticancer agents", *Nucleosides, Nucleotides & Nucleic Acids*, 22(5-8):577-81 (2003).

Gryaznov, S. et al., "Telomerase inhibitors—oligonucleotide phosphoramidates as potential therapeutic agents", *Nucleosides, Nucleotides & Nucleic Acids*, 20(4-7): 401-410 (2001).

Herbert, B.S. et al., "Oligonucleotide N3'—>P5' phosphoramidates as efficient telomerase inhibitors", *Oncogene*, 21(4):638-42 (2002).

Illum, J.,"Nasal drug delivery—possibilities, problems and solutions", *Control Release*, 87(1-3):187-198 (2003).

Kim, M. et al., "A low threshold level of expression of mutant-template telomerase RNA inhibits human tumor cell proliferation", *Proc. Natl. Acad. Sci. USA*, 98(14):7982-7987 (2001).

Komata, T. et al. "Combination therapy of malignant glioma cells with 2-5A-antisense telomerase RNA and recombinant adenovirus p53", *Gene Therapy*, 7(24):2071-2079 (2000).

Komata, T. et al., "Telomerase as a therapeutic target for malignant gliomas", *Oncogene*, 21(4):656-663 (2002).

Pruzan et al., "Allosteric inhibitors of telomerase: oligonucleotide N3'—>P5' phosphoramidates", *Nucleic Acids Research*, 30:559-568 (2002).

You, Y. et al., "Antisense telomerase RNA inhibits the growth of human glioma cells in vitro and in vivo", *International Journal of Oncology*, 28(5):1225-1232, (2006).

Behl, "Nasal drug delivery: unique opportunities and challenges", Behl Holding Corp., Inc., Slide presentation dated Jun. 9, 2005.

Corbo et al., "Drug absorption through mucosal membranes: effect of mucosal route and penetrant hydrophilicity", Pharm. Res., vol. 6, No. 10, pp. 848-852 (1989) *Abstract only*.

Draghia et al., "Gene delivery into the central nervuos system by nasal installation in rats", Gene Ther., vol. 2, No. 6, pp. 418-423 (1995) *Abstract only*.

Fisher et al., "The effect of molecular size on the nasal absorption of water-soluble compounds in the albino rat", J. Pharm. Pharmacol., vol. 39, No. 5, pp. 357-362 (1987).

Sakane et al., "Transport of cephalexin to the cerebrospinal fluid directly from the nasal cavity", J. Pharm. Pharmacol., vol. 43, No. 6, pp. 449-451 (1991).

Sakane et al., "The transport of a drug to the cerebrospinal fluid directly from the nasal cavity: the relation to the lipophilicity of the drug", vol. 39, No. 9, pp. 2456-2458 (1991) *Abstract only*.

Shingaki et al., "Transnasal delivery of anticancer drugs to the brain tumor: A new strategy for brain tumor chemotherapy", Drug Delivery System, vol. 14, No. 5, pp. 365-371 (1999) *English abstract only*.

Vyas et al., "Intranasal drug delivery for brain targeting", Current Drug Delivery, vol. 2 No. 2, pp. 165-175 (2005).

Wang et al., "Profiles of methotrexate in blood and CSF following intranasal and intravenous administration to rats", Int. J. Pharm., vol. 263, No. 1-2, pp. 1-7 (2003).

Wang et al., "Intranasal Delivery of Methotrexate to the Brain in Rats Bypassing the Blood-Brain Barrier", Drug Delivery Technology, vol. 4, No. 1, 16 pages (2004).

Wang et al., "Study on brain targeting of raltitrexed following intranasal administration in rats", Cancer Chemother. Pharmacol., vol. 57, No. 1, pp. 97-104 (2006).

\* cited by examiner

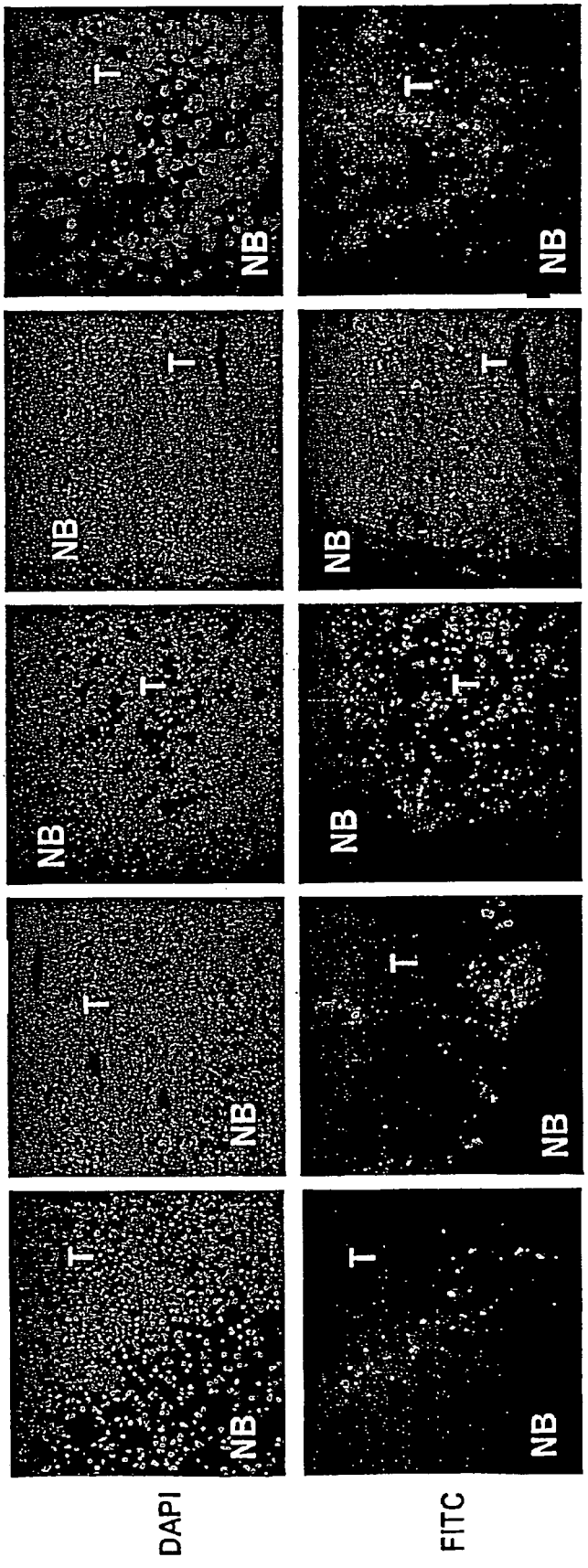

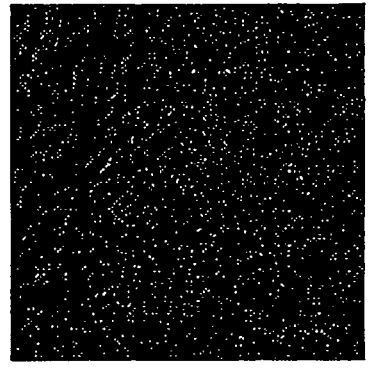
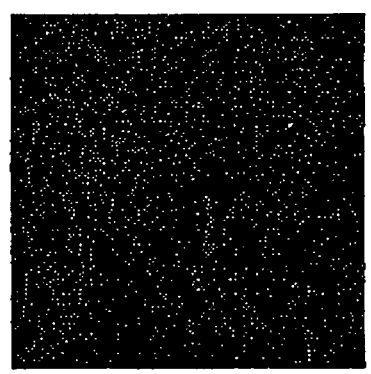
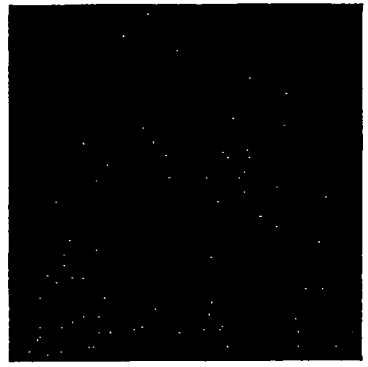
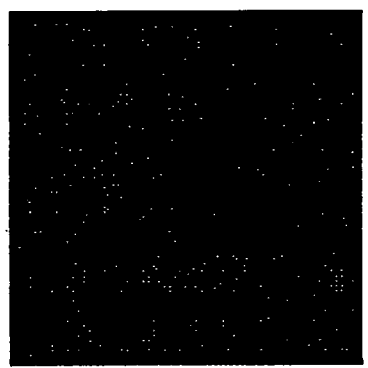
Fig. 2B Contralateral normal brain
Fig. 2A Adjacent normal brain surrounding tumor
Fig. 2D
Fig. 2C
DAPI
FITC

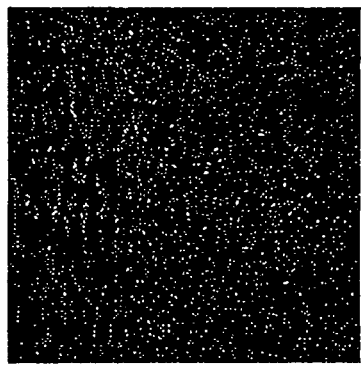
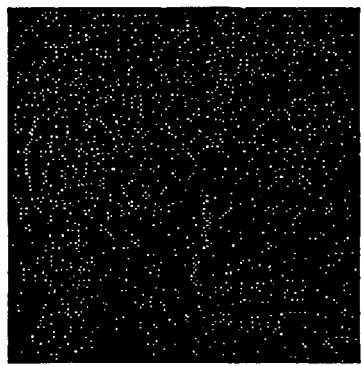
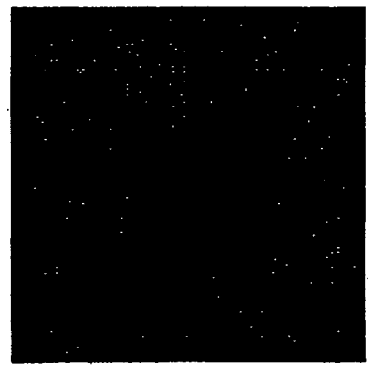
Fig. 3A Ipsilateral brain
Fig. 3B Contralateral brain
Fig. 3C
Fig. 3D
DAPI
FITC

GRN 163

Control

NB: normal brain, T: tumor

CNS-TUMOR TREATMENT METHOD AND COMPOSITION

This application is the National Stage of International Application No. PCT/US2007/009839 filed on Apr. 23, 2007, which claims the benefit of U.S. Provisional Application No. 60/794,873 filed on Apr. 24, 2006.

FIELD OF THE INVENTION

The present invention is directed to treatment of tumors of the central nervous system (CNS), specifically, to inhibition of tumor growth or cancer-cell proliferation, by treatment with a telomerase inhibitor administered intranasally, and to an aerosol composition and delivery device for use in the method.

BACKGROUND

Malignant gliomas are the most common malignant primary tumors in the human brain, and the 5-year survival rate for patients with glioblastoma multiforme (GBM), the most aggressive form of malignant glioma, is less than 5% even with surgery followed by radiation therapy and chemotherapy (Surawicz, Davis et al. 1998; Legler, Ries et al. 1999), CBTRUS: Central Brain Tumor Registry of The United States, http://www.cbtrus.org/2005-2006/tables/2006.table19.pdf, accessed 24 Jan. 2006). Although there have been numerous attempts to develop improved therapies for these tumors in the past 30 years, delivery of drugs to tumors of the central nervous system remains a major problem, mainly due to difficulty penetrating the blood-brain barrier (BBB).

One technique that has been proposed recently for enhancing therapy effectiveness in tumors of the CNS is convection enhanced delivery (CED), which is a continuous infusion that uses a convective (versus diffusive) flow to drive the therapeutic agent throughout a larger region of tissue (Huynh, Deen et al. 2006). CED is currently is under investigation for brain tumor treatment in several institutions, including the University of California, San Francisco (UCSF) (Kawakami, Kawakami et al. 2004; Lidar, Mardor et al. 2004; Mamot, Nguyen et al. 2004; Ozawa, Gryaznov et al. 2004; Ozawa, Santos et al. 2004; Saito, Bringas et al. 2004; Boiardi, Eoli et al. 2005; MacKay, Deen et al. 2005; Ozawa, Afzal et al., 2005; Saito, Krauze et al. 2006). However, CED requires the use of potentially risky surgical procedures to position the catheter into the patients' brain parenchyma (Bobo, Laske et al. 1994; Groothuis 2000). Another obstacle for brain tumor therapy is that most chemotherapeutic agents do not discriminate between tumor cells and normal tissues, thus toxicity becomes a major problem. Clearly, there is great need for new therapeutic strategies that will provide efficient drug delivery to brain tumors, using drugs that preferentially target brain tumors while sparing normal tissues from damage.

It would therefore be desirable to provide a method for treating tumors of the CNS that (i) does not require surgical intervention, (ii) is relatively specific in targeting tumor cells of the CNS, and (iii) is effective in reducing cell growth in tumors of the CNS.

SUMMARY OF THE INVENTION

The invention includes, in one aspect, a method for treating a tumor of the central nervous system in a subject, by intranasally administering to the subject, an amount of a telomerase inhibitor effective to inhibit growth of the tumor in the subject.

An exemplary telomerase inhibitor is an oligonucleotide having nuclease-resistant intersubunit linkages, and an oligonucleotide sequence effective to bind by sequence-specific hybridization to the RNA component of human telomerase (hTR), including binding to particular regions of hTR such as the template region, or effective to inhibit synthesis of hTERT proteins. The internucleoside linkages in the oligonucleotide may be N3'→P5' phosphoramidate and N3'→P5' thiophosphoramidate linkages. The oligonucleotide may be 10-20 bases in length, and include the sequence identified by SEQ ID NO: 12. One exemplary telomerase inhibitor for use in the invention is GRN163.

The method may be applied in the treatment of a variety of tumors of the CNS, including malignant gliomas, such as glioblastoma multiforme (GBM). The method may be part of a combined therapy in which a second anti-tumor drug is administered before, during, or following administration of the telomerase inhibitor, or in conjunction with surgical removal of a tumor, or in conjunction with radiation or radionuclide therapy.

Where the telomerase inhibitor is an oligonucleotide having N3'→P5' phosphoramidate or N3'→P5' thiophosphoramidate backbone linkages, and a sequence effective to bind by hybridization to hTR, the invention may include a method for localizing a small-molecule diagnostic or therapeutic agent, such as a fluorescent moiety, in a CNS tumor, by intranasally administering a conjugate of the oligonucleotide and the small molecule. The small-molecule compound may be linked at either end of the oligonucleotide, such as the 5-end thiophosphate or the 3'-end amine of a thiophosphoramidate-linked oligonucleotide.

In another aspect, the invention includes an intranasal delivery device, comprising (a) a telomerase inhibitor, and (b) a delivery apparatus for producing an aerosol of the telomerase inhibitor suitable for intranasal delivery. In exemplary embodiments, the telomerase inhibitor is an oligonucleotide inhibitor as described above. The delivery apparatus may be effective to aerosolize the telomerase inhibitor in an aerosol-particle carrier, such as a dry powder carrier, an aqueous droplet carrier, and a volatile organic (propellant) carrier. Alternatively, compound delivery may be via dropper for applying drops of the compound in the subject's nose, or delivered in a gel or capsule form.

Also disclosed is an aerosol of a telomerase inhibitor in a particle carrier, in an amount suitable for intranasal delivery in a human subject. A therapeutic dose of the telomerase inhibitor may be carried in an aerosol-particle carrier, such as a dry powder carrier, an aqueous droplet carrier, and a volatile organic (propellant) carrier. In exemplary embodiments, the telomerase inhibitor in the aerosol is an oligonucleotide inhibitor as described above. Also disclosed is a gel or capsule form of an oligonucleotide telomerase inhibitor suitable for intranasal delivery in a therapeutic dose.

These and other objects and features of the invention will become more fully apparent when the following detailed description of the invention is read in conjunction with the accompanying drawings.

BRIEF DESCRIPTION OF THE DRAWINGS

FIGS. 1A-1E show the distribution of DAPI-labeled brain cells in brain sections of athymic rats containing gliobastoma intracerebral xenografts, and FIGS. 1F-1J, the distribution of FITC-labeled GRN163 in the same sections, at the time periods indicated after administration of GRN163. In these and the following figures, "T" designates tumor, "NB" designates normal brain.

FIGS. 2A-2B show the distribution of DAPI-labeled brain cells in brain sections from areas of adjacent normal brain surrounding the tumor (2A) and contralateral brain (2B), and FIGS. 2C-2D, the absence of FITC-labeled GRN163 in the same sections.

FIGS. 3A-3B show the distribution of DAPI-labeled brain cells in brain sections from ipsilateral brain (3A) and contralateral brain (3B) as indicated, and FIGS. 3C-3D, the absence of FITC-labeled GRN163 in the same sections.

DETAILED DESCRIPTION OF THE INVENTION

I. Definitions

Figure 4B:
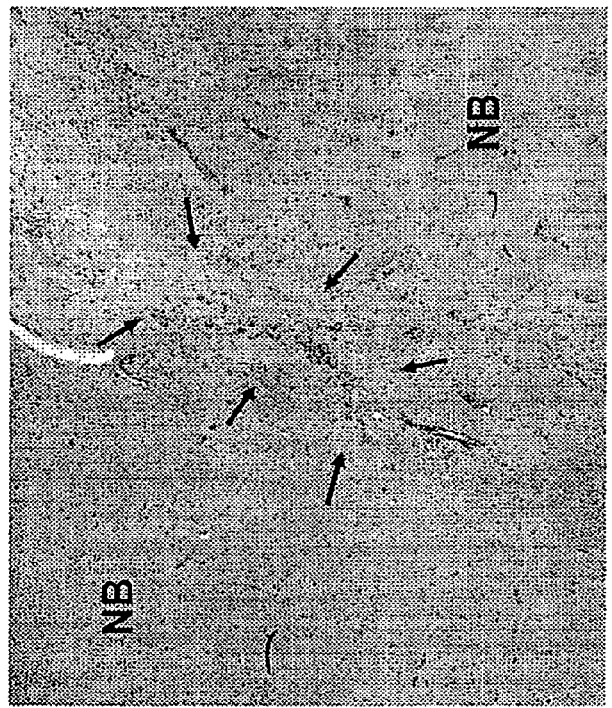
FIGS. 4A and 4B show photomicrographs of histological sections of brain from athymic rats transplanted with human U-251 MG brain tumor cells with no treatment (4A) and treatment with GRN163 (4B), in accordance with the invention.

The terms below have the following meanings unless indicated otherwise.

A "polynucleotide" or "oligonucleotide" refers to a ribose and/or deoxyribose nucleoside subunit polymer or oligomer having between about 2 and about 200 contiguous subunits. The nucleoside subunits can be joined by a variety of intersubunit linkages, including, but not limited to, phosphodiester, phosphotriester, methylphosphonate, P3'→N5' phosphoramidate, N3'→P5' phosphoramidate, N3'→'P5' thiophosphoramidate, and phosphorothioate linkages. The term also includes such polymers or oligomers having modifications, known to one skilled in the art, to the sugar (e.g., 2' substitutions), the base (see the definition of "nucleoside" below), and the 3' and 5' termini. In embodiments where the oligonucleotide moiety includes a plurality of intersubunit linkages, each linkage may be formed using the same chemistry, or a mixture of linkage chemistries may be used. When an oligonucleotide is represented by a sequence of letters, such as "ATGUCCTG," it will be understood that the nucleotides are in 5'→3' order from left to right. Representation of the base sequence of the oligonucleotide in this manner does not imply the use of any particular type of internucleoside subunit in the oligonucleotide.

The term "nucleoside" includes the natural nucleosides, including 2'-deoxy and 2'-hydroxyl forms, e.g., as described in Kornberg and Baker, DNA Replication, 2nd Ed. (Freeman, San Francisco, 1992), and analogs. "Analogs", in reference to nucleosides, includes synthetic nucleosides having modified nucleobase moieties (see definition of "nucleobase" below) and/or modified sugar moieties, e.g., described generally by Scheit, *Nucleotide Analogs* (John Wiley, New York, 1980). Such analogs include synthetic nucleosides designed to enhance binding properties, e.g., stability, specificity, or the like, such as disclosed by Uhlmann and Peyman (*Chemical Reviews* 90:543-584, 1990).

A "nucleobase" includes (i) native DNA and RNA nucleobases (uracil, thymine, adenine, guanine, and cytosine), (ii) modified nucleobases or nucleobase analogs (e.g., 5-methylcytosine, 5-bromouracil, or inosine) and (iii) nucleobase analogs. A nucleobase analog is a compound whose molecular structure mimics that of a typical DNA or RNA base.

The term "substituted" refers to a compound which has been modified by the exchange of one atom or moiety for another, typically substitution of hydrogen by a different atom or moiety. In particular, the term is used in reference to halogenated hydrocarbons and fatty acids, particularly those in which one or more hydrogen atoms are substituted with fluorine.

An "hTR template inhibitor" is a compound that blocks the template region (the region spanning nucleotides 30-67 of SEQ ID NO: 1 herein) of the RNA component of human telomerase, thereby inhibiting the activity of the enzyme. The inhibitor is typically an oligonucleotide that is able to hybridize to this region. Preferably, the oligonucleotide includes a sequence effective to hybridize to a more specific portion of this region having sequence 5'-CUAACCCUAAC-3' and spanning nucleotides 46-56 of SEQ ID NO: 1 herein.

A telomerase inhibitor is said to "inhibit the growth of a tumor in a subject" if the rate of growth of the tumor in the subject is less than that observed in the absence of the compound, as evidenced, for example, by reduction in tumor mass, reduction the rate of tumor growth, or increase survival rate of a subject being treated.

An oligonucleotide having a "nuclease-resistant linkages" refers to one whose backbone has subunit linkages that are substantially resistant to nuclease cleavage, in non-hybridized or hybridized form; by common extracellular and intracellular nucleases in the body; that is, the oligonucleotide shows little or no nuclease cleavage under normal nuclease conditions in the body to which the oligonucleotide is exposed. The N3'→P5' phosphoramidate (NP) or N3'→P5' thiophosphoramidate (NPS) linkages described below are nuclease resistant.

II. Treatment of CNS Tumors by Intranasal Delivery of a Telomerase Inhibitor

Human telomerase is a specialized ribonucleoprotein reverse transcriptase containing essential RNA (hTR) and protein (hTERT) subunits (Greider and Blackburn 1985; Feng, Funk et al. 1995; Nakamura, Morin et al. 1997). Telomerase stabilizes telomere length by adding the d(TTAGGG)n telomeric repeats to the ends of the chromosomes and is responsible for cellular immortalization of cancers (Kim, Piatyszek et al. 1994; Shay and Wright 1996; Holt, Wright et a/1997; Blackburn 2001). Since telomerase is expressed in essentially all cancer cells, but not in normal somatic cells (Kim, Piatyszek et al 1994; Hiyama, Hiyama et a/1995), cancer cell DNA is continuously extended or maintained by telomerase to compensate for the lost telomeric repeats, and as a result the cells become immortalized. Telomerase is expressed in the vast majority of primary brain tumors, but not in normal brain tissues. For instance 89% of GBMs express telomerase, whereas normal brain tissues do not (Langford, Piatyszek et a/1995; Morii, Tanaka et a/1997; Chong, Lam et al. 1998; Le, Zhu et al. 1998; Sano, Asai et a/1998).

In the present method, it has been discovered that tumors of the CNS may be effectively treated by intranasal administration of a telomerase inhibitor to a subject. Intranasal delivery provides a practical, noninvasive method of bypassing the blood-brain barrier (BBB) to deliver a telomerase inhibitor to the CNS because of the unique anatomic connection provided by the olfactory and trigeminal nerves between the nasal mucosa and the central nervous system (CNS) that has evolved to sense odors and other chemical stimuli.

The use of intranasal delivery as a route for drug delivery has several advantages in drug delivering to the CNS, such as rapid delivery to the CNS, bypassing the BBB, avoidance of hepatic first-pass drug metabolism, and elimination of the need for systemic delivery, thereby reducing unwanted systemic side effects. Intranasal delivery also provides painless and convenient self-administration by patients—features that encourage its use as a viable strategy for delivering therapeutic agents into the CNS.

A. Small Molecule Telomerase Inhibitors

The telomerase inhibitor used in the present treatment method may be a small-molecule telomerase inhibitor, or an oligonucleotide inhibitor of the type described in Section B below. Small-molecule inhibiters include BRACO19 ((9-(4-(N,N-dimethylamino)phenylamino)-3,6-bis(3-pyrrolodino propionamido)acridine (see *Mol. Pharmacol.* 61(5):1154-62, 2002); DODC (diethyloxadicarbocyanine), and telomestatin (Shin-ya et al. *J. Am. Chem. Soc.* 123 (6): 1262-1263, 2001) These compounds may act as G-quad stabilizers, which promote the formation of an inactive G-quad configuration in the RNA component of telomerase. Other small molecule inhibitors of telomerase include BIBR1532 (2-[(E)-3-naphthen-2-yl but-2-enoylamino]benzoic acid) (see Ward & Autexier, *Mol. Pharmacol.* 68:779-786, 2005; also *J. Biol. Chem.* 277 (18):15566-72, 2002); AZT and other nucleoside analogs, such as ddG and ara-G (see, for example, U.S. Pat. Nos. 5,695,932 and 6,368,789), and certain thiopyridine, benzo[b]thiophene, and pyrido[b]thiophene derivatives, described by Gaeta et al. in U.S. Pat. Nos. 5,767,278, 5,770,613, 5,863, 936, 5,656,638 and 5,760,062. One example is 3-chlorobenzo [b]thiophene-2-carboxy-2'-[(2,5-dichlorophenyl amino)thia] hydrazine, described in U.S. Pat. No. 5,760,062.

B. Oligonucleotide-Based Telomerase Inhibitors

The genes encoding both the protein and RNA components of human telomerase have been cloned and sequenced (see U.S. Pat. Nos. 6,261,836 and 5,583,016, respectively, both of which are incorporated herein by reference). Oligonucleotides can be targeted against the mRNA encoding the telomerase protein component (the human form of which is known as human telomerase reverse transcriptase, or hTERT). The design of antisense, ribozyme or small interfering RNA (siRNA) agents to inhibit or cause the destruction of mRNAs is well known (see, for example, Lebedeva, I, et al. Annual Review of Pharmacology and Toxicology, Vol. 41: 403-419, April 2001; Macejak, D, et al., Journal of Virology, Vol. 73 (9): p. 7745-7751, September 1999, and Zeng, Y. et al., PNAS Vol. 100 (17) pp. 9779-9784, 2003) and such agents may be designed to target the hTERT mRNA and thereby inhibit production of hTERT protein in a target cell, such as a cancer cell (see, for example, U.S. Pat. Nos. 6,444,650 and 6,331, 399).

Alternatively, the oligonucleotide telomerase inhibitor may be directed against the RNA component of telomerase (hTR). The nucleotide sequence of the RNA component of human telomerase (hTR) is shown in the Sequence Listing below (SEQ ID NO: 1), in the 5'→3' direction. The sequence is shown using the standard abbreviations for ribonucleotides; those of skill in the art will recognize that the sequence also represents the sequence of the cDNA, in which the ribonucleotides are replaced by deoxyribonucleotides, with uridine (U) being replaced by thymidine (T). The region of hTR defined by nucleotides 30-67 of SEQ ID NO: 1 is located at the active site of the holoenzyme, and is herein referred to as the template region. In particular, the sequence spanning nucleotides 46-56 (5'-CUAACCCUAAC-3'), is complementary to a telomeric sequence composed of about one-and-two-thirds telomeric repeat units and this essential sequence functions as the template for the addition of the telomeric repeats that telomerase adds to the chromosome ends (see e.g. Chen et al., *Cell* 100:503-514, 2000; Kim et al., *Proc. Nat. Acad. Sci. USA* 98(14):7982-7987, 2001).

Oligonucleotides targeting hTR (that is, the RNA component of the enzyme) act as inhibitors of telomerase enzyme activity by blocking or otherwise interfering with the interaction of hTR with the hTERT protein, which interaction is necessary for telomerase function. See, for example, Villeponteau et al., U.S. Pat. No. 6,548,298. A detailed description of oligonucleotides targeting hTR is presented in Gryaznov et al., *Nucleosides, Nucleotides & Nucleic Acids* 20(4-7): 401-401, 2001.

A preferred target region of hTR is the template region, spanning nucleotides 30-67 of SEQ ID NO:1. Oligonucleotides targeting this region are referred to herein as "hTR template inhibitors" (see e.g. Herbert et al., *Oncogene* 21(4): 63842 (2002).) Preferably, such an oligonucleotide includes a sequence which is complementary or near-complementary to some portion of the 11-nucleotide sequence 5'-CUAAC-CCUAAC-3', spanning nucleotides 46-56 of SEQ ID NO:1.

Another preferred target region is the region spanning nucleotides 137-179 of hTR (see Pruzan et al., *Nucl. Acids Research,* 30:559-568, 2002). Within this region, the sequence spanning 141-153 is a preferred target. PCT publication WO 98/28442 describes the use of oligonucleotides of at least 7 nucleotides in length to inhibit telomerase, where the oligonucleotides are designed to be complementary to accessible portions of the hTR sequence outside of the template region, including nucleotides 137-196, 290-319, and 350-380 of hTR. Preferred hTR targeting sequence are given below, and identified by SEQ ID NOS: 2-22.

The region of the therapeutic oligonucleotide that is targeted to the hTR sequence is preferably exactly complementary to the corresponding hTR sequence. While mismatches may be tolerated in certain instances, they are expected to decrease the specificity and activity of the resultant oligonucleotide conjugate. In particular embodiments, the base sequence of the oligonucleotide is thus selected to include a sequence of at least 5 nucleotides exactly complementary to the hTR target, and enhanced telomerase inhibition may be obtained if increasing lengths of complementary sequence are employed, such as at least 8, at least 10, at least 12, at least 13 or at least 15 nucleotides exactly complementary to the hTR target. In other embodiments, the sequence of the oligonucleotide includes a sequence of from at least 5 to 20, from at least 8 to 20, from at least 10 to 20 or from at least 10 to 15 nucleotides exactly complementary to the hTR target sequence.

Optimal telomerase inhibitory activity may be obtained when the full length of the oligonucleotide is selected to be complementary to the hTR target sequence. However, it is not necessary that the full length of the oligonucleotide is exactly complementary to the target sequence, and the oligonucleotide sequence may include regions that are not complementary to the target sequence. Such regions may be added, for example, to confer other properties on the compound, such as sequences that facilitate purification. Alternatively, an oligonucleotide may include multiple repeats of a sequence complementary to an hTR target sequence.

If the oligonucleotide is to include regions that are not complementary to the target sequence, such regions are typically positioned at one or both of the 5' or 3' termini. Exemplary sequences targeting human telomerase RNA (hTR) include the ones given in Table 1 below.

The internucleoside linkages in the oligonucleotide may include any of the available oligonucleotide chemistries, e.g.

phosphodiester, phosphotriester, methylphosphonate, P3'→N5' phosphoramidate, N3'→P5' phosphoramidate, N3'→P5' thiophosphoramidate, and phosphorothioate. Typically, but not necessarily, all of the internucleoside linkages within the oligonucleotide will be of the same type, although the oligonucleotide component may be synthesized using a mixture of different linkages.

In preferred embodiments, the oligonucleotide has at least one N3'→P5' phosphoramidate (NP) or N3'→P5' thiophosphoramidate (NPS) linkage, which linkage may be represented by the structure: 3'—(—NH—P(=O)(—XR)—O—)-5', wherein X is O (for NP linkages) or S (for NPS linkages) and R is selected from the group consisting of hydrogen, alkyl, and aryl; and pharmaceutically acceptable salts thereof, when XR is OH or SH. More preferably, the oligonucleotide includes all NP or, most preferably, all NPS linkages.

A particularly preferred sequence for an hTR template inhibitor oligonucleotide is the sequence complementary to nucleotides 42-54 of SEQ ID NO: 12 above. The oligonucleotide having this sequence (TAGGGTTAGACA) and N3'→P5' thiophosphoramidate (NPS) linkages is designated herein as GRN163. See, for example, Asai et al., *Cancer Research* 63:3931-3939 (2003); Gryaznov et al., *Nucleosides Nucleotides Nucleic Acids* 22(5-8):577-81 (2003).

TABLE 1

| hTR Targeting Sequence | Region of SEQ ID NO: 1 | SEQ ID NO: |
|---|---|---|
| ACATTTTTGTTTGCTCTAG | 160-179 | 2 |
| GCTCTAGAATGAACGGTGGAAGGCGGCAGG | 137-166 | 3 |
| GTGGAGGCGGCAGG | 137-151 | 4 |
| GGAAGGCGGCAGG | 137-149 | 5 |
| GTGGAAGGCGGCA | 139-151 | 6 |
| GTGGAAGGCGG | 141-151 | 7 |
| CGGTGGAAGGCGG | 141-153 | 8 |
| ACGGTGGAAGGCG | 142-154 | 9 |
| AACGGTGGAAGGCGGC | 143-155 | 10 |
| ATGAACGGTGGAAGGCGG | 144-158 | 11 |

TABLE 1-continued

| hTR Targeting Sequence | Region of SEQ ID NO: 1 | SEQ ID NO: |
|---|---|---|
| TAGGGTTAGACAA | 42-54 | 12 |
| CAGTTAGGGTTAG | 46-58 | 13 |
| TAGGGTTAGACA | 42-53 | 14 |
| TAGGGTTAGAC | 42-52 | 15 |
| GTTAGGGTTAG | 46-56 | 16 |
| GTTAGGGTTAGAC | 44-56 | 17 |
| GTTAGGGTTAGACAA | 42-56 | 18 |
| GGGTTAGAC | 44-52 | 19 |
| CAGTTAGGG | 50-58 | 20 |
| CCCTTCTCAGTT | 54-65 | 21 |
| CGCCCTTCTCAG | 56-67 | 22 |

As shown in Table 2 below, this oligonucleotide (first row of table) inhibits telomerase at low concentrations in a biochemical assay (FlashPlate™; see Experimental Section). An alternative 13-mer, having the sequence CAGTTAGGGTTAG, complementary to nucleotides 46-58 of SEQ ID NO: 1 (fifth row of table), showed near-equivalent activity in the FlashPlate™ assay. The corresponding NP-linked oligonucleotide, and shorter (11- and 12-mer) oligonucleotides targeting the same region (complementary to nucleotides 42-53 and 42-42, respectively, of SEQ ID NO: 1), showed moderate activity. The effect is clearly sequence-specific, as shown by the mismatch and non-targeting sequences in the table.

The oligonucleotide GRN163 administered alone has shown inhibitory activity in vitro in cell culture, including epidermoid carcinoma, breast epithelium, renal carcinoma, renal adenocarcinoma, pancreatic, brain, colon, prostate, leukemia, lymphoma, myeloma, epidermal, cervical, ovarian and liver cancer cells; and to a variety of tumors in animal model systems, where the compound has been administered parenterally, e.g., intravenously, subcutaneously, or intraperitoneally.

TABLE 2

Inhibition of Telomerase by NPS Oligonucleotides: Biochemical (FlashPlate) Assay

| Sequence, 5' to 3' | Description | $IC_{50}$, nM |
|---|---|---|
| TAGGGTTAGACAA SEQ ID NO: 12 | 13-mer (GRN163) | 0.045 ± 0.007 |
| TAGG<u>T</u>GTA<u>AG</u>CAA (SEQ ID NO: 23) | Mismatch of GRN163 sequence | 80 ± 31 |
| TTGTCTAACCCTA (SEQ ID NO: 24) | Complement of GRN163 sequence | 1000 ± 46 |
| TAGGGTTAGACAA ATCCCAATCTGTT | Duplex of GRN163 sequence | 8.9 ± 3.0 |
| CAGTTAGGGTTAG (SEQ ID NO: 13) | Alternative targeting 13-mer | 0.049 ± 0.007 |

TABLE 2-continued

Inhibition of Telomerase by NPS Oligonucleotides: Biochemical (FlashPlate) Assay

| Sequence, 5' to 3' | Description | IC$_{50}$, nM |
|---|---|---|
| TAGGGTTAGACA (SEQ ID NO: 14) | 12-mer; truncation of GRN163 sequence | 0.36 ± 0.2 |
| TAGGGTTAGAC (SEQ ID NO: 15) | 11-mer; truncation of GRN163 sequence | 0.85 ± 0.35 |
| GTTAGGGTTAG (SEQ ID NO: 16) | Alternative targeting 11-mer | 0.51 ± 0.13 |
| GTTGAGTGTAG (SEQ ID NO: 25) | Mismatch of alternative targeting 11-mer | 177 ± 93 |
| TAGGGTTAGACAA (SEQ ID NO: 12) | 13-mer (GRN163 sequence) with NP backbone | 0.7 ± 0.1 |
| TAGGTGTAAGCAA (SEQ ID NO: 2) | Mismatch of GRN163 sequence with NP backbone | >1000 |
| TTAGGG (SEQ ID NO: 26) | Telomere repeat unit | >1000 |
| TTTTTTTTTT (SEQ ID NO: 27) | Oligo-T 10-mer | >1000 |

The oligonucleotide telomerase inhibitor may be modified or derivatized, e.g., to alter its pharmacokinetic properties in the CNS, or to provide co-delivery of a small molecule therapeutic or diagnostic agent to a tumor site in the CNS. As will be seen below, an oligonucleotide telomerase inhibitor, such as GRN163, when modified to carry the fluorescent marker FITC, provides a method for detecting the distribution of the oligonucleotide in tumor sites in an animal-model brain. In human diagnostics, a small-molecule diagnostic agent may be a radionuclide or magnetic imaging agent that allows detection of tumor sites in the brain, and/or confirmation that the telomerase inhibitor is localizing at the CNS tumor site, e.g., for purposes of monitoring dosing and treatment efficacy. A radionuclide carried on the oligonucleotide may be a therapeutic radionuclide, such as phosphorus-32, strontium-89, rhenium-186, or zctinium-225. For non-phosphorus radionuclides, the agent may be carried in a suitable chelating moiety covalently attached to the oligonucleotide.

Alternatively, the small molecule may be an anti-tumor agent currently in use or under clinical investigation for treating tumors of the CNS, such as CPT-11, Tenozolomide, Thalidomide, TNP470, Marimastat, Tamoxifen, and Bryostatin, or an anti-inflammatory or anti-convulsant agent also used in the treatment of tumors of the CNS.

The small molecule can be coupled to the oligonucleotide by known coupling methods and linkers, such as through an amide, ester or anhydride linker that allows for intracellular release of the agent within the tumor cells. The small-molecule compound may be linked at either end of the oligonucleotide, such as the 5-end thiophosphate or the 3'-end amine of a thiophosphoramidate-linked oligonucleotide, according to known coupling methods. Specific approaches for attaching small molecules to a terminus of an NP or NPS oligonucleotide include those described in US Appn. Pubn. No. 2005/0113325, which is incorporated herein by reference.

More generally, it will be understood that the treatment method of the invention can be carried out in combination with other therapeutic modalities, including surgical removal of tumor tissue, radiation therapy, radionuclide therapy, immunotherapy, and therapy involving a second anti-tumor agent, where the mode of administration of the second therapeutic agent or modality may be by known route, consistent with established clinical protocols, but where the therapeutic dose or dosing of the second agent or modality may be lower or less frequent than when used alone.

C. Treatment Method

In practicing the method of the invention, a subject having a CNS tumor is initially identified as a candidate for the therapy. The tumor may be a primary CNS tumor, or a metastatic tumor formed by cancer cells that start elsewhere in the body. The tumor may be a blastoma, a malignant tumor whose cells have undeveloped (embryonic) characteristics; for example, medulloblastoma or glioblastoma multiforme; a glioma, the general name for a tumor that arises from the supportive tissue of the brain; for example, astrocytoma or oligodendroglioma, or a tumor type that originates outside the CNS, such as a carcinoma, or sarcoma. The tumor is detected and localized by known means, including MRI and radio-agent imaging. The tumor is also graded as to degree of malignancy, based on the tumor's tendency to spread (infiltrate), its growth rate, and its similarity to normal cells. The treatment may typically follow a surgical procedure to remove or debulk the tumor sites from the CNS, where surgical removal or resection is possible. The method of the invention may also be used to treat other tumors to which the telomerase inhibitor may be delivered by intra-nasal delivery, including olfactory and nasal tumors.

In an exemplary treatment method, the subject is administered the telomerase inhibitor, e.g., GRN163, by intranasal administration, on a predetermined schedule, e.g., once every 6-12 hours, once per day, 2-3 times/per week, or every week or longer. In appropriate patients, the telomerase inhibitor may be self-administered by the patient. The dose and dosing schedule and treatment duration for administering the telomerase inhibitor will depend on various factors including, but not limited to, whether the tumor has been debulked by surgical intervention, the type of the tumor, the age and general health of the patient, the aggressiveness of disease progression, the telomere length and telomerase activity of the diseased cells to be treated.

The therapeutic agents are administered to a subject, such as a human patient, in a formulation and in an amount effective to achieve a clinically desirable result. For the treatment of a CNS tumor, desirable results include reduction in tumor mass (as determined; e.g., by radiography, radionucleotide scan, CAT scan, or MRI), reduction in the rate of tumor growth and improvement in quality of life (as determined by clinical assessment, e.g., Karnofsky score), increased time to progression, disease-free survival and overall survival.

The amount of telomerase inhibitor per dose and the number of doses required to achieve such effects will vary depending on many factors including the disease indication, characteristics of the patient being treated and the mode of administration. Typically, the aerosol formulation will be such as to provide a local concentration at the CNS tumor site of between 1 nM and 100 µM. This local concentration can be achieved, at an uptake efficiency of about 50% of the intranasally administered aerosol, in an aerosol dose containing between about 0.1 to 100 µmoles/dose, more preferably 0.5 to 50 µmoles/dose, such as an exemplary dose of between about 2-40 µmoles/dose, of the telomerase inhibitor. Intranasal delivery devices for producing aerosol doses in this range are described in the Section III below. At doses above about 30-40 µmoles, an oligonucleotide telomerase inhibitor may have to be formulated in powder or gel form in order to meet acceptable solubility and/or viscosity constraints.

An exemplary treatment method in an animal model for GBM is detailed below in Sections D-G of the Experimental section. Briefly, the method involved intranasal delivery of the telomerase inhibitor, GRN163, to athymic rats having intracerebral (i.c.) tumors. Initially, the distribution of fluorescence after intranasal delivery of 3'-fluorescein isothiocyanate (FITC)-labeled GRN163 was investigated. Two animals were euthanized at selected points in time from 0.5 to 24 hours after initiating intranasal delivery of FITC-labeled GRN163, and their brains and tumors were examined for the presence of the compound using a fluorescence microscope. FIGS. 1A-1E show the staining of cells with the fluorescence compound DAPI in the five sections, where areas of tumor cells (T) and normal brain (NB) cells are indicated. FIGS. 1F-1J show FITC labeling by GRN163-FITC in the same cells. As seen in the latter figures, fluorescence was detected in tumor cells at the edge of the tumors at 0.5 hours after intranasal delivery and was visible throughout the tumors at 4 hours. Fluorescence remained visible in the tumor cells 24 hours after the delivery. Little or no fluorescence was detected in normal brain cells in the adjacent area surrounding the tumor (FIGS. 2C and 2D), and no fluorescence was detected in the ipsilateral and contralateral brain tissue (FIGS. 3C and 3D). No apparent toxicity or behavioral abnormalities were observed during the course of this study in any of the rats receiving FITC-labeled GRN163 via intranasal delivery, and there was no detectable fluorescence from GRN163 in lung or liver tissue obtained from these animals (data not shown).

In an initial treatment method, a small number of rats bearing human GBM i.c. xenografts we treated with daily intranasal doses of phosphate-buffered saline (PBS)-Control, (n=5), or 0.21 (n=4), 0.325 (n=5) and 0.65 (n=3) µmol GRN163 for 12 days. GRN163 prolonged the median survival from day 36 in PBS-Controls to day 48 in 0.21 µmol, to day 47 in 0.325 µmol, and to day 99 in 0.65 µmol GRN163-treatment groups (data not shown).

Figure 4A:
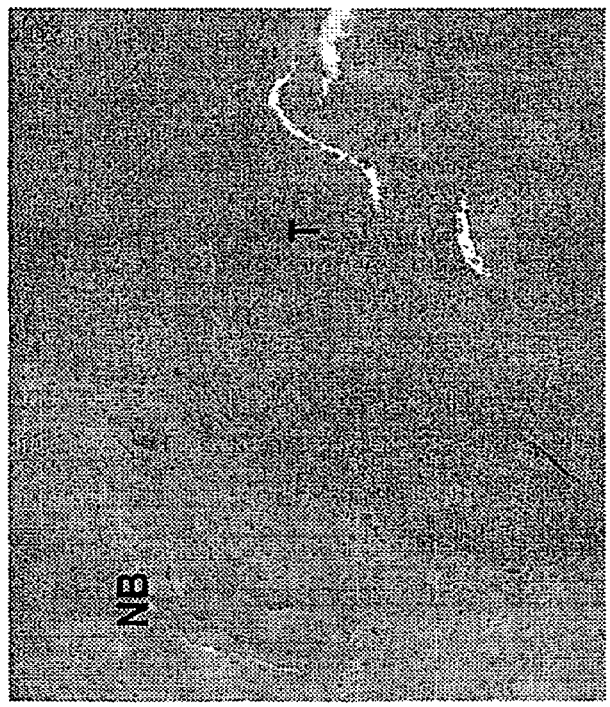

In a further treatment method, rats bearing human GBM i.c. xenografts were treated with daily intranasal doses PBS (control, n=10), 0.65 µmol of GRN163 (n=10), or mismatched-sequence control thio-phosphoramidate oligonucleotides (MM-Control). As seen in Table 3, survival timed in PBS-Control and MM-Control animals ranged from 32 to 43 days; median survival of both control groups was 35 days. GRN163 treatment significantly prolonged the median survival of animals to day 75.5 (p<0.01), and 3 GRN163-treated rats were alive and showed no neurological symptoms at the time of euthanasia on day 104. There was no evidence of tumor at the original implantation site in any of these 3 rats (FIG. 4B). However, all the other rats that were euthanized due to neurological symptoms had a large tumor at the site of implantation (FIG. 4A). Fluorescein staining at 4 hours after final delivery of the 12-day treatment confirmed FITC-GRN163 uptake in the tumor (data not shown).

TABLE 3

Days post-tumor implantation to euthanization for tumor efficacy study after completion of a 12 day intranasal delivery of GRN163**

|  | PBS Control Group 0 µmol (n = 10)* | MM Control Group 0.65 µmol (n = 10) | GRN163 Group 0.65 µmol (n = 10) |
|---|---|---|---|
|  | Day 32 | Day 32 | Day 33 |
|  | Day 33 | Day 32 | Day 35 |
|  | Day 35 | Day 32 | Day 47 |
|  | Day 35 | Day 33 | Day 63 |
|  | Day 35 | Day 35 | Day 70 |
|  | Day 35 | Day 35 | Day 81 |
|  | Day 36 | Day 35 | Day 81 |
|  | Day 38 | Day 36 | Cured (day 104)* |
|  | Day 39 | Day 36 | Cured (day 104)* |
|  | Day 43 | Day 36 | Cured (day 104)* |
| Median Survival | Day 35 | Day 35 | Day 75.5 |

*Rats with neurological symptoms were euthanized on day 32 to 43. Rats showing no symptoms (those that were cured) by day 104 were euthanized, and no evidence of tumor was observed histologically.
*Rats received 65 µl PBS per day.

Figures 5A, 5B, 5C:
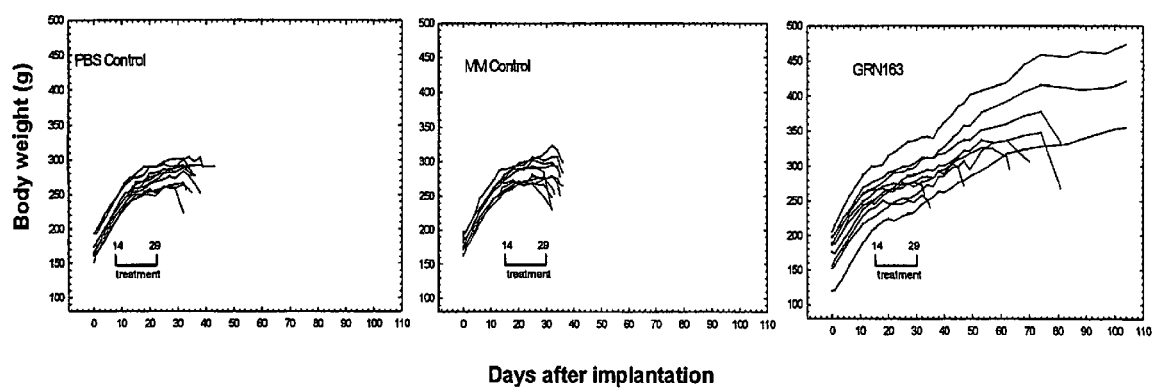
FIGS. 5A-5C are plots showing body weights and survival rates in athymnic rats transplanted with human U-251 MG brain tumor cells at time zero, for PBS control (5A); a sequence-mismatch oligonucleotide control (5B), and treatment with GRN163 (5C).

Importantly, no apparent toxicity or behavioral abnormalities were observed during the 12-day treatment with GRN163. All rats gained weight during the treatment period, and rats with symptoms of tumors began to lose weight a few days before being euthanized (FIGS. 5A-5C). An autopsy was performed on 4 rats selected randomly from each of the three groups that were euthanized when they showed symptoms of a tumor. All organs were grossly normal, and lungs, livers, hearts, spleens, and kidneys were normal on histological examination (data not shown).

The oligonucleotide-distribution study noted above with respect to FIG. 1 demonstrates that FITC-labeled GRN163 is detected in tumor cells 0.5 hour after intranasal administration (FIG. 1F), indicating the intranasal GRN163 rapidly bypassed the BBB and reached the brain tumor. The rapid uptake of GRN163 into the brain by intranasal delivery is consistent with extraneuronal transport of GRN163 via the olfactory and trigeminal pathways. Further, once intranasal GRN163 reached the brain, this compound showed tumor specific distribution at all time points studied (0.5 to 24 hours) and achieved the highest concentration within the tumor at 4 hours after delivery (FIG. 11), indicating favorable tumor uptake and extensive parenchymal penetration and retention of intranasal GRN163. Intranasally administered GRN163 shows very little or no accumulation in adjacent normal brain tissues surrounding the tumor (FIGS. 1F-1J, 2C-2D, and 3C-3D). These findings indicate that intranasal GRN163 is rapidly delivered along the olfactory and trigeminal neural pathways throughout normal brain parenchyma, achieving efficient distribution and targeting in brain tumor cells. The animals receiving a daily dose of 0.65 µmol of GRN163 administered intranasally for 12 days showed no apparent toxicity.

III. Intranasal Delivery Devices and Aerosols

The invention includes, in one aspect, an intranasal delivery device designed for delivery of a metered dose of a telomerase inhibitor. As noted above, when the selected telomerase inhibitor is an oligonucleotide such as GRN163, the metered dose for intranasal delivery preferably contains between about 0.1 to 100 µmoles, e.g., 2-40 µmoles of oligonucleotide telomerase inhibitor. The metered dose and may be formed as a dry-powder aerosol, an atomized aerosol of aqueous droplets containing the oligonucleotide in solute or suspension form, or an aerosol formed of the compound carried in a volatile organic (propellant) carrier. In other embodiments, a solution of the telomerase inhibitor may be applied in liquid-drop form in the subject's nose, e.g., by a defined-volume eye dropper, or a gel or capsule containing the compound may be placed in the nose. Dry powder inhalers for creating a metered dose of a dry-powder form of a therapeutic compound are well known. Methods for formulating drugs in dry-powder form suitable for intranasal delivery by inhalation are well known. See, for example, U.S. Pat. Nos. 7,022,311; 7,001,818; 6,794,357; 6,780,508, 6,475,523, and references cited therein, all of which are incorporated herein by reference. In one method, the compound for delivery, such as the oligonucleotide telomerase inhibitor GRN163, is formulated with carrier material, such as a low-molecular weight polymer, physiological salts or carbohydrates or the like, and dried and milled to a suitable particle size, e.g., in the range of a few microns. The dry-powder material is packaged for single-dose delivery, e.g., in a magazine containing a plurality of such doses. Devices for delivering dry-powder formulations in metered dose suitable for intranasal administration are well known. In this embodiment of the invention, the device is designed to produce a metered-dose, dry-powder aerosol containing a dose of oligonucleotide telomerase inhibitor suitable for intranasal administration.

Alternatively, a metered dose of the telomerase inhibitor in an aerosol suitable for intranasal delivery may be composed of the telomerase inhibitor entrained or dissolved in a suitable volatile propellant, such as is well known in the art. In this approach, the telomerase inhibitor is carried in a suitable propellant in the delivery device, and the device is designed to release, with each activation, an amount of entrained compound corresponding to a dose of the telomerase inhibitor compound suitable for intranasal administration in the treatment of a CNS tumor.

In still another approach, the delivery device includes a reservoir for an aqueous solution or suspension of the telomerase inhibitor compound. The device, when activated, produces a volume of aerosol corresponding to a metered dose of the compound.

Devices suitable for intra-nasal delivery compounds are discussed in Aggarwal et al., AlliedSci 29: 201-205, 2004; Illum, J. Control Release 87:843-845, 2003; and Djupesland et al Laryngoscope 116: 466-472, 2006. Such devices are commercially available, e.g., from B.D. Medical (Franklin Lakes, N.J.), Kurve Technology (Bothell, Wash.), and the OptiMist device from OptiNose AS, Oslo, Norway. pgd@optinose.no.

IV. Measurement of Telomere Length, Telomerase Activity, and/or Cell Proliferation When employing a therapeutic regimen that involves administration of a telomerase inhibitor, it may be useful to determine telomere length and/or telomerase activity in a cell or tissue sample. These parameters can be measured by assays known in the art. Telomere length can be measured by a flow cytometry method using fluorescence in situ hybridization, referred to as flow FISH (see e.g. M. Hultdin et al., Nucleic Acids Res. 26(16):3651-6, 1998; N. Rufer et al., Nature Biotechnology 16:743-7, 1998). Other methods include terminal restriction fragment (TRF) analysis, in which genomic DNA is digested with a restriction enzyme having a four-base recognition sequence not present in telomere repeat sequences, and the restriction fragments are separated according to size, e.g. by gel electrophoresis. See, for example, U.S. Pat. No. 5,489,508 (West et al.) and Harley et al., Nature 345:458, 1990. The West et al. patent also describes methods of measuring telomere length by an "anchored terminal primer" method and by a modified Maxam-Gilbert reaction.

In addition, a more rapid response to a telomerase inhibiting agent may be predicted for tumor cells having shorter telomeric DNA, although telomerase has been shown to have other inhibitory effects independent of telomere length. (e.g. Stewart et al., PNAS 99:12606, 2002; Zhu et al., PNAS 93:6091, 1996; Rubaiyat et al., Oncogene 24(8):1320, 2005); and Folini et al., Curr. Pharm. Design 11(9):1105, 2005).

The TRAP assay (see Experimental, below) is a standard method for measuring telomerase activity in a cell extract system (Kim et al., Science 266:2011, 1997; Weinrich et al., Nature Genetics 17:498, 1997). Briefly, this assay measures the amount of nucleotides incorporated into elongation products (polynucleotides) formed by nucleotide addition to a labeled telomerase substrate or primer. The TRAP assay is described in detail in U.S. Pat. Nos. 5,629,154, 5,837,453 and 5,863,726, and its use in testing the activity of telomerase inhibitory compounds is described in various publications, including WO 01/18015. In addition, the following kits are available commercially for research purposes for measuring telomerase activity: TRAPeze™ XK Telomerase Detection Kit (Intergen Co., Purchase N.Y.); and TeloTAGGG Telomerase PCR ELISA plus (Roche Diagnostics, Indianapolis Ind.).

The anticancer activity of the telomerase inhibitor can be evaluated using standard in vitro and in vivo assays. A preferred protocol for such growth curve assays is the short term cell viability assay described in Asai et al. (2003, cited above).

EXPERIMENTAL

A. Preparation and Lipid Conjugation of Oligonucleotide N3'→P5' Phosphoramidates or N3'→P5' Thiophosphoramidates These compounds may be prepared as described, for example, in McCurdy et al., Tetrahedron Letters 38:207-210 (1997) or Pongracz & Gryaznov, Tetrahedron Letters 49:7661-7664 (1999). The starting 3'-amino nucleoside monomers may be prepared as described in Nelson et al., J. Org. Chem. 62:7278-7287 (1997) or by the methods described in Gryaznov et al., US Appn. Pubn. No. 2006/0009636.

B. FlashPlate™ Assay

This assay was carried out essentially as described in Asai et al., Cancer Research, 63:3931 3939 (2003). Briefly, the assay detects and/or measures telomerase activity by measuring the addition of TTAGGG telomeric repeats to a biotinylated telomerase substrate primer. The biotinylated products are captured on streptavidin-coated microtiter plates, and an oligonucleotide probe complementary to 3.5 telomere repeats, labeled with 33P, is used for measuring telomerase products. Unbound probe is removed by washing, and the amount of probe annealing to the captured telomerase products is determined by scintillation counting.

C. TRAP Assay

The ability of a compound to increase or inhibit telomerase activity in a cell can be determined using the TRAP (Telomeric Repeat Amplification Protocol) assay, which is described, for example, in Kim et al., U.S. Pat. No. 5,629,154; Harley et al., U.S. Pat. No. 5,891,639; and Harley et al., PCT Pubn. No. WO 2005/000245. Briefly, telomerase-expressing tumor cell lines are incubated with test compositions, lysed, and treated with a labeled oligonucleotide telomerase substrate, appropriate primers, and internal standard for quantitation purposes. Depending on the telomerase activity of the medium, telomer repeats will be added to the substrate, to form telomerase extended products. The mixture is incubated at room temperature, followed by multiple cycles of PCR. The mixture is separated on a gel, and labeled extension product is detected and quantitated via comparison with the internal standard.

D. Cell Cultures and Animals

U-251 MG human GBM cells were obtained from the Department of Neurological Surgery Tissue Bank at UCSF. Cells were maintained as exponentially growing monolayers in complete minimal essential medium (CMEM) consisting of Eagle's minimal essential medium supplemented with 10% fetal calf serum and non-essential amino acids. Cells were cultured at 37° C. in a humidified atmosphere containing 95% air and 5% $CO_2$. Cells were seeded into culture flasks 2 days before tumor implantation. For implantation, cells were harvested by trypsinization, washed once, and resuspended in Hanks' balanced salt solution (HBSS) without $Ca^{2+}$ and $Mg^{2+}$.

Six-week-old male athymic rats (rnu/rnu, homozygous) were purchased from Harlan (Indianapolis, Ind.) and housed under aseptic conditions, which included filtered air and sterilized food, water, bedding, and cages. All protocols were approved by the UCSF Institutional Animal Care and Use Committee.

E. U-251 MG Human Glioblastoma Intracarebral Tumor Model

Tumor cells were implanted into the brains of athymic rats as previously described (Ozawa et al., 2002). Briefly, rats were anesthetized with an intraperitoneal injection of ketamine (60 mg/kg) and xylazine (7.5 mg/kg) and injected slowly with the U-251 MG cell suspension ($2 \times 10^6$ cells in 10 µl HBSS) into the right caudate-putamen using an implantable guide-screw system. Typically, this procedure results in a 100% tumor take and a median survival time of animals of ~35 days after tumor implantation (Ozawa, Wang et al. 2002).

F. Intranasal Delivery of GRN163 in Athymic Rats

Tumor bearing rats were anesthetized with inhalation of 2~2.5% isoflurane and placed in a supine-position in an anesthesia chamber. Six µl of PBS containing GRN163 (0.65 µmol/65 µl) were administered intranasally as drops with a small pipette every 2 minutes, for a total of 20 minutes, into alternating sides of the nasal cavity. This was followed by administration of 5 µl of GRN163 for the last dose. A total volume of 65 µl was delivered into the nasal cavity. After delivery, animals were removed from the anesthesia chamber and they regained consciousness and were ambulatory within 3 minutes.

G. Time Course Distribution Study of GRN163 in Athymic Rats

On day 25 after implantation of U-251 MG cells, when the i.c. tumors were approximately 50 mg in size as determined from earlier growth curves (Ozawa, Wang et al. 2002), 65 µl of PBS containing FITC-labeled GRN163 was delivered over 20 minutes into the nasal cavity as described above. Two rats each were euthanized at 0.5, 1, 2.5, 4 and 24 hours after delivery by perfusion with PBS, and their brains containing tumors were dissected and frozen in ethanol and dry ice. The brains were sectioned coronally, and 10 µm thick sections were placed on microscope slides. Ten to 15 µl of mounting medium containing 2 µg/ml of 4' 6-Diamidine-2' Phenylindole dihydrochloride (DAPI, Boehringer Mannheim Biochemica, Mannheim, Germany) were added over the sections, and a cover glass was placed over the samples. The resulting slides were immediately viewed and photographed using a fluorescent microscope (Carl Zeiss MicroImaging, Thornwood, N.Y.). An ultraviolet-light transmission filter was used for DAPI to visualize the nuclei of cells. A blue-light transmission filter was used for FITC to visualize the green signal that indicates cells containing oligonucleotides.

H. Treatment of Tumors in Athymic Rats with Intranasal GRN163

Tumor bearing rats were treated intranasally with daily doses of 0.65 µmole of GRN163 or MM Control in PBS, or a control solution of PBS alone (PBS-Control) for 12 days (with weekends off) over a 3 week-period. Treatment was initiated on day 14 when i.c. tumors were approximately 20 mg in size. The investigators treating the animals were fully blinded with regard to treatment. All rats were monitored every day and were euthanized when they exhibited neurological symptoms indicative of impending death (Ozawa, Wang et al. 2002). Their brains were collected for histological examination using standard hematoxylin and eosin (H & E) staining.

Although the invention has been described with respect to particular embodiments and applications, those skilled in the art will appreciate the range of applications and methods of the invention disclosed herein.

---

It is claimed:

1. A method for treating a tumor of the central nervous system in a subject, comprising intranasally administering to the subject, an amount of an oligonucleotide telomerase inhibitor effective to inhibit growth of the tumor in the subject;
   wherein the oligonucleotide telomerase inhibitor is 10-20 bases in length and comprises nuclease-resistant intersubunit linkages and an oligonucleotide sequence effective to bind by sequence-specific hybridization to the RNA component of human telomerase (hTR).

2. The method of claim 1, which further includes administering to the subject, before, during, or following administration of the telomerase inhibitor, a second anti-tumor agent.

3. The method of claim 1, wherein the telomerase inhibitor is effective to bind by sequence-specific hybridization to the template region of hTR.

4. The method of claim 3, wherein the internucleoside linkages in the oligonucleotide are selected from N3'→P5' phosphoramidate and N3'→P5' thiophosphoramidate linkages.

5. The method of claim 3, wherein the oligonucleotide includes the sequence identified by SEQ ID NO:12.

6. The method of claim 5, wherein the internucleoside linkages in the oligonucleotide are selected from N3'→P5' phosphoramidate and N3'→P5' thiophosphoramidate linkages.

7. The method of claim 6, wherein the telomerase inhibitor is the compound GRN163.

8. The method of claim 1, which further includes selecting for treatment, a patient having a malignant glioma.

* * * * *

SEQUENCE LISTING

<160> NUMBER OF SEQ ID NOS: 27

<210> SEQ ID NO 1

<211> LENGTH: 554
<212> TYPE: RNA
<213> ORGANISM: Homo sapiens

<400> SEQUENCE: 1

```
ggguugcgga ggugggccu gggaggggug guggccauuu uuugucuaac ccuaacugag    60
aagggcguag gcgccgugcu uuugcucccc gcgcgcuguu uuucucgcug acuuucagcg   120
ggcggaaaag ccucggccug ccgccuucca ccguucauuc uagagcaaac aaaaaaugug   180
agcugcuggc ccguucgccu cccggggacc ugcggcgggu cgccugccca gccccgaac    240 cccgccugga gccgcggucg gcccggggcu ucuccggagg cacccacugc caccgcgaag   300
aguugggcuc ugucagccgc gggucucucg ggggcgaggg cgagguucac cguuucaggc   360
cgcaggaaga ggaacggagc gaguccgcc gcggcgcgau ucccugagcu gugggacgug    420
cacccaggac ucggcucaca caugcaguuc gcuuccugu ugguggggg aacgccgauc    480 gugcgcaucc gucacccuc gccggcagug ggggcuugug aacccccaaa ccugacugac   540
ugggccagug ugcu                                                     554
```

<210> SEQ ID NO 2
<211> LENGTH: 20
<212> TYPE: DNA
<213> ORGANISM: Homo sapiens

<400> SEQUENCE: 2

```
acatttttg tttgctctag                                                 20
```

<210> SEQ ID NO 3
<211> LENGTH: 30
<212> TYPE: DNA
<213> ORGANISM: Homo sapiens

<400> SEQUENCE: 3

```
gctctagaat gaacggtgga aggcggcagg                                     30
```

<210> SEQ ID NO 4
<211> LENGTH: 14
<212> TYPE: DNA
<213> ORGANISM: Homo sapiens

<400> SEQUENCE: 4

```
gtggaggcgg cagg                                                      14
```

<210> SEQ ID NO 5
<211> LENGTH: 13
<212> TYPE: DNA
<213> ORGANISM: Homo sapiens

<400> SEQUENCE: 5

```
ggaaggcggc agg                                                       13
```

<210> SEQ ID NO 6
<211> LENGTH: 13
<212> TYPE: DNA
<213> ORGANISM: Homo sapiens

<400> SEQUENCE: 6

```
gtggaaggcg gca                                                       13
```

<210> SEQ ID NO 7
<211> LENGTH: 11
<212> TYPE: DNA

<213> ORGANISM: Homo sapiens

<400> SEQUENCE: 7
gtggaaggcg g                                                          11

<210> SEQ ID NO 8
<211> LENGTH: 13
<212> TYPE: DNA
<213> ORGANISM: Homo sapiens

<400> SEQUENCE: 8
cggtggaagg cgg                                                        13

<210> SEQ ID NO 9
<211> LENGTH: 13
<212> TYPE: DNA
<213> ORGANISM: Homo sapiens

<400> SEQUENCE: 9
acggtggaag gcg                                                        13

<210> SEQ ID NO 10
<211> LENGTH: 16
<212> TYPE: DNA
<213> ORGANISM: Homo sapiens

<400> SEQUENCE: 10
aacggtggaa ggcggc                                                     16

<210> SEQ ID NO 11
<211> LENGTH: 18
<212> TYPE: DNA
<213> ORGANISM: Homo sapiens

<400> SEQUENCE: 11
atgaacggtg gaaggcgg                                                   18

<210> SEQ ID NO 12
<211> LENGTH: 13
<212> TYPE: DNA
<213> ORGANISM: Homo sapiens

<400> SEQUENCE: 12
tagggttaga caa                                                        13

<210> SEQ ID NO 13
<211> LENGTH: 13
<212> TYPE: DNA
<213> ORGANISM: Homo sapiens

<400> SEQUENCE: 13
cagttagggt tag                                                        13

<210> SEQ ID NO 14
<211> LENGTH: 12
<212> TYPE: DNA
<213> ORGANISM: Homo sapiens

<400> SEQUENCE: 14
tagggttaga ca                                                         12

<210> SEQ ID NO 15
<211> LENGTH: 11
<212> TYPE: DNA

<213> ORGANISM: Homo sapiens

<400> SEQUENCE: 15
tagggttaga c                                                                11

<210> SEQ ID NO 16
<211> LENGTH: 11
<212> TYPE: DNA
<213> ORGANISM: Homo sapiens

<400> SEQUENCE: 16
gttagggtta g                                                                11

<210> SEQ ID NO 17
<211> LENGTH: 13
<212> TYPE: DNA
<213> ORGANISM: Homo sapiens

<400> SEQUENCE: 17
gttagggtta gac                                                              13

<210> SEQ ID NO 18
<211> LENGTH: 15
<212> TYPE: DNA
<213> ORGANISM: Homo sapiens

<400> SEQUENCE: 18
gttagggtta gacaa                                                            15

<210> SEQ ID NO 19
<211> LENGTH: 9
<212> TYPE: DNA
<213> ORGANISM: Homo sapiens

<400> SEQUENCE: 19 gggttagac                                                                    9

<210> SEQ ID NO 20
<211> LENGTH: 9
<212> TYPE: DNA
<213> ORGANISM: Homo sapiens

<400> SEQUENCE: 20 cagttaggg                                                                    9

<210> SEQ ID NO 21
<211> LENGTH: 12
<212> TYPE: DNA
<213> ORGANISM: Homo sapiens

<400> SEQUENCE: 21
cccttctcag tt                                                               12

<210> SEQ ID NO 22
<211> LENGTH: 12
<212> TYPE: DNA
<213> ORGANISM: Homo sapiens

<400> SEQUENCE: 22
cgcccttctc ag                                                               12

<210> SEQ ID NO 23
<211> LENGTH: 13
<212> TYPE: DNA

```
<213> ORGANISM: Homo sapiens

<400> SEQUENCE: 23
taggtgtaag caa                                                          13

<210> SEQ ID NO 24
<211> LENGTH: 13
<212> TYPE: DNA
<213> ORGANISM: Homo sapiens

<400> SEQUENCE: 24
ttgtctaacc cta                                                          13

<210> SEQ ID NO 25
<211> LENGTH: 11
<212> TYPE: DNA
<213> ORGANISM: Homo sapiens

<400> SEQUENCE: 25
gttgagtgta g                                                            11

<210> SEQ ID NO 26
<211> LENGTH: 6
<212> TYPE: DNA
<213> ORGANISM: Homo sapiens

<400> SEQUENCE: 26 ttaggg                                                                   6

<210> SEQ ID NO 27
<211> LENGTH: 10
<212> TYPE: DNA
<213> ORGANISM: Homo sapiens

<400> SEQUENCE: 27
tttttttttt                                                              10
```